(12) United States Patent
Jutras

(10) Patent No.: US 10,918,836 B2
(45) Date of Patent: Feb. 16, 2021

(54) CATHETER PROTECTOR

(71) Applicant: CONCEPT H2-ITEX INC., Brossard (CA)

(72) Inventor: Monique Jutras, Brossard (CA)

(73) Assignee: Concept H2-ITEX Inc., Brossard (CA)

( * ) Notice: Subject to any disclaimer, the term of this patent is extended or adjusted under 35 U.S.C. 154(b) by 238 days.

(21) Appl. No.: 16/100,614

(22) Filed: Aug. 10, 2018

(65) Prior Publication Data

US 2019/0046772 A1 Feb. 14, 2019

Related U.S. Application Data

(60) Provisional application No. 62/543,539, filed on Aug. 10, 2017.

(51) Int. Cl.
*A61M 25/02* (2006.01)
*A41D 13/08* (2006.01)
*A61F 15/00* (2006.01)

(52) U.S. Cl.
CPC ........... *A61M 25/02* (2013.01); *A61F 15/004* (2013.01); *A41D 13/08* (2013.01); *A61M 2025/0213* (2013.01); *A61M 2025/0246* (2013.01); *A61M 2025/0253* (2013.01)

(58) Field of Classification Search
CPC .......... A61M 25/02; A61M 2025/0206; A61M 2025/0213; A41D 13/08; A61B 46/22; A61F 5/0118; A61F 5/013; A61F 5/0588; A61F 5/05866; A61F 5/3723; A61F 5/373; A61F 2013/00093; A61F 2013/0104

USPC ................ 2/16, 59; 128/856, 877, 878, 892; 602/62–64, 20, 23
See application file for complete search history.

(56) References Cited

U.S. PATENT DOCUMENTS

| 4,470,410 A | * | 9/1984 | Elliott ..................... A61M 5/52 128/877 |
| 4,495,659 A | * | 1/1985 | Madnick .............. A41D 13/081 2/66 |
| 5,174,305 A | | 12/1992 | Childs |
| 5,181,274 A | | 1/1993 | Defiore |
| 5,190,530 A | * | 3/1993 | Greeff ................... A61M 25/02 604/174 |
| 5,415,642 A | | 5/1995 | Shepherd |

(Continued)

FOREIGN PATENT DOCUMENTS

| EP | 2982355 A1 | 2/2016 |
| WO | 2013014319 A1 | 1/2013 |

*Primary Examiner* — Gloria M Hale
(74) *Attorney, Agent, or Firm* — Benoit & Cote, Inc.

(57) ABSTRACT

There is described a protective cover for a body member of a patient having a catheter inserted therein at a catheter insertion point. A sleeve wraps around the body part over the catheter, and comprises a sleeve body covering a substantial surface of the body member. The sleeve body is made of a material that is non-rigid and flexible, to adapt to the surface of the body member. An openable window covers and provides access to the catheter when the protective cover is worn, the openable window being openable with respect to the sleeve body and fastenable by a waterproof fastener. The inner surface of the openable window is for securing an antiseptic agent, wherein the inner surface of the openable window is applied onto the catheter insertion point when the openable window is closed. The protective cover is free of any rigid member.

13 Claims, 16 Drawing Sheets

(56) References Cited

U.S. PATENT DOCUMENTS

| | | | |
|---|---|---|---|
| 5,720,713 A | 2/1998 | Hutchinson | |
| 6,222,090 B1 | 4/2001 | Weston | |
| 6,267,115 B1 | 7/2001 | Marshel | |
| 6,276,364 B1 | 8/2001 | Warner | |
| 6,663,582 B2 * | 12/2003 | Ballard | A61F 5/0104 602/64 |
| 6,832,611 B2 | 12/2004 | Altman | |
| 7,077,142 B1 * | 7/2006 | Barany | A61F 5/3761 128/877 |
| 7,182,088 B2 * | 2/2007 | Jenkins | A61M 5/52 128/878 |
| 7,658,719 B2 | 2/2010 | Bockol et al. | |
| 7,913,320 B2 * | 3/2011 | Grissom | A61M 25/02 2/59 |
| 8,615,814 B1 * | 12/2013 | Hawkins | A41D 13/081 2/66 |
| 9,227,039 B1 * | 1/2016 | Williams, Sr. | A61M 25/02 |
| 9,913,320 B2 * | 3/2018 | Garvey | G01P 13/00 |
| 9,993,621 B2 * | 6/2018 | Bouchard | A61M 25/02 |
| 10,188,541 B2 * | 1/2019 | Combs | A61F 5/05858 |
| 10,583,274 B2 * | 3/2020 | Bienvenu | A61F 5/01 |
| 2003/0196242 A1 | 10/2003 | Korkor | |
| 2006/0264794 A1 * | 11/2006 | Fuchs | A61F 5/0104 602/26 |
| 2007/0083163 A1 * | 4/2007 | Rydell | A61M 25/02 604/174 |
| 2007/0088281 A1 | 4/2007 | Ritchey | |
| 2008/0071224 A1 * | 3/2008 | Forsyth | A61M 25/02 604/179 |
| 2008/0208130 A1 * | 8/2008 | Furman | A61M 25/02 604/164.08 |
| 2011/0301544 A1 * | 12/2011 | Dixon | A61M 25/02 604/179 |
| 2012/0144547 A1 | 6/2012 | Collins et al. | |
| 2013/0317445 A1 | 11/2013 | Steer | |
| 2017/0136216 A1 | 5/2017 | Razdan et al. | |

* cited by examiner

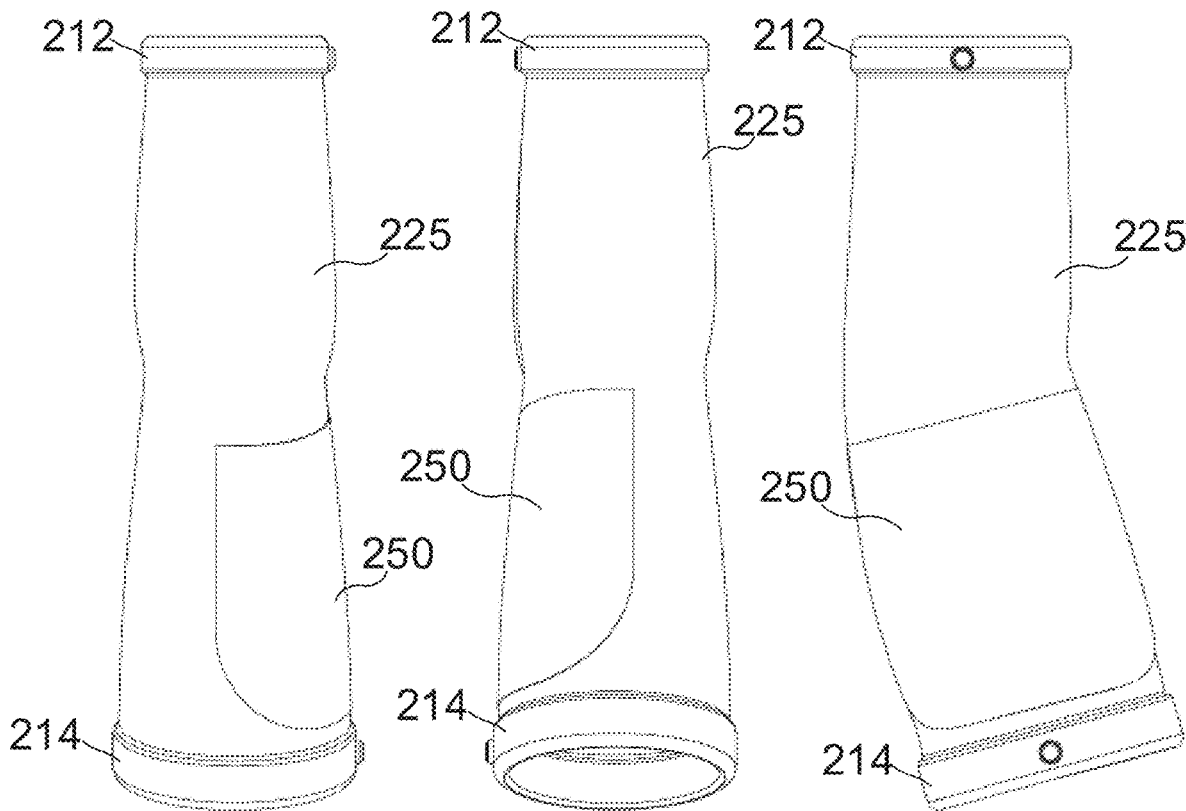

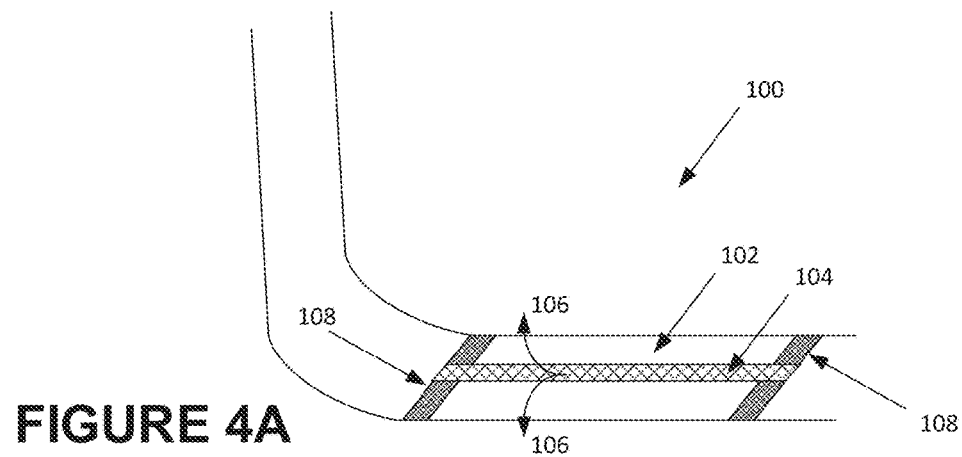
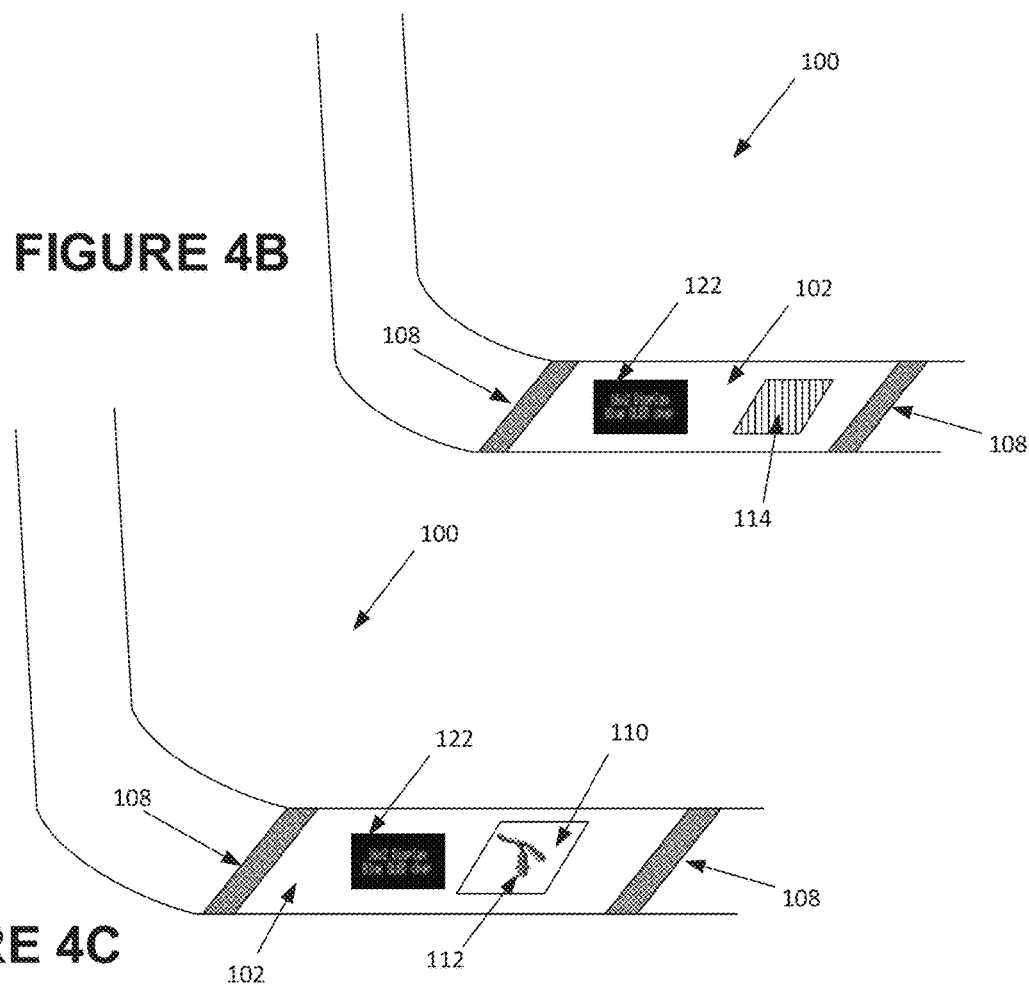

CATHETER PROTECTOR

CROSS-REFERENCE TO RELATED APPLICATIONS

This application claims benefit of U.S. provisional patent application 62/543,539, filed Aug. 10, 2017, which is hereby incorporated herein by reference in its entirety.

BACKGROUND

(a) Field

The subject matter disclosed generally relates to a medical protector for protecting an area of the body where a permanent catheter is inserted.

(b) Related Prior Art

Venous catheters are widely used in medicine for providing permanent or temporary access to the blood. Such access may be intended for a variety of uses including fluid delivery, monitoring pressure, administering medications/antibiotics and the like, blood sampling, stem cell collection, etc.

The catheter may be provided in a variety of locations within the body including on the arm, the neck for accessing the central jugular vein, on the chest for accessing the subclavian vein or on the hand.

FIG. 1 is an example of a conventional venous catheter installed on the arm of the patient.

While convenient for providing access to and from the blood, such catheters do complicate the life of the patient due to the high maintenance they require and the need to keep them clean and away from dirt, sweat, humidity, dust etc. in order to prevent infections.

In other words, these catheters prevent the patients using them from practicing and enjoying their basic day to day activities and needs such as but not limited to: showering, sports, showing up in public without having people stare at the tubes inserted in their skin, etc.

There are protectors for catheter sites that protect the local environment around the catheter site to prevent water running on the catheter site and/or to prevent infections. These local protectors have a specific purpose for protection (e.g., waterproofness, infection prevention, etc.) and are convenient for use in hospitals. They usually allow people to shower while preventing infections on the local surrounding of the catheter entry point. An example of such a local protector is a Tegaderm™ protector.

However, the local protectors as used in hospitals are also a nuisance in themselves. Their purpose does not usually go beyond being waterproof for the catheter site and holding the catheter tubing. They are usually provided as a rigid cap (US20130317445A1), a large plaster (U.S. Pat. No. 6,832,611B2), a pocket (U.S. Pat. No. 7,658,719B2), or a loose envelope (U.S. Pat. No. 6,276,364B1). This means that are usually bulky or do not fit well on people bodies, hence they are easy to hit or displace accidentally and do not provide discretion when the person is in public. Local protectors of catheter sites are therefore not adapted to the multiple and varied conditions encountered in everyday life, especially at home.

Therefore, there is a need in the market for catheter protector which is aesthetically appealing and at the same time addresses the above problems, i.e., that provides versatility for everyday life.

SUMMARY

The present embodiments describe a protector that is used to protect and conveniently hide the catheter site for everyday life. If a local protector as used in nursing is provided on the catheter site, the protector as described herein below can be used as a complement over this local protector (and surrounding the environment thereof) for additional protection and greater discretion and ease of use for the varied conditions of everyday life that the local protector alone cannot reasonably withstand.

According to an aspect of the invention, there is provided a protective cover for a body member of a patient having a catheter inserted therein at a catheter insertion point, the protective cover comprising a sleeve to wrap around the body part over the catheter, the sleeve comprising:

a sleeve body covering a substantial surface of the body member of the patient including a joint, the sleeve body being made of a material that is non-rigid, flexible and elastic, the sleeve body conforming to the surface of the body member of the patient that is covered;

an openable window for covering and providing access to the catheter when the protective cover is worn, the openable window being openable with respect to the sleeve body and defining an openable contour portion being fastenable to the sleeve body by a waterproof fastener along the openable contour portion which is waterproof along a whole length thereof, the openable window defining an inner surface and comprising an area on the inner surface for securing an antiseptic agent, wherein the inner surface of the openable window is applied onto the catheter insertion point when the openable window is closed, wherein the inner surface is brought away from the catheter insertion point when the openable window is opened, a proximal band and a distal band to be provided around the body member at a proximal end and a distal end of the sleeve body, respectively, each of the proximal band and the distal band being inflatable to press against the body member and provide waterproofness to the proximal end and to the distal end of the sleeve body, wherein the protective cover is free of any rigid member covering the body member.

According to an embodiment, there is further provided a cutout pocket provided inside the openable window for receiving the catheter when the protective cover is worn by the patient, the cutout pocket comprising padding.

According to another aspect of the invention, there is provided protective cover for a body member of a patient having a catheter inserted therein at a catheter insertion point, the protective cover comprising a sleeve to wrap around the body part over the catheter, the sleeve comprising:

a sleeve body covering a substantial surface of the body member of the patient including a joint, the sleeve body being made of a material that is non-rigid and flexible, the sleeve body conforming to the surface of the body member of the patient that is covered;

an openable window for covering and providing access to the catheter when the protective cover is worn, the openable window being openable with respect to the sleeve body, the openable window defining an inner surface which is applied onto the catheter insertion point when the openable window is closed, and brought away from the catheter insertion point when the openable window is opened.

According to an embodiment, the openable window comprises an area on the inner surface for securing an antiseptic agent.

According to an embodiment, the openable window defines an openable contour portion being fastenable to the sleeve body by a waterproof fastener along the openable contour portion which is waterproof along a whole length thereof, the waterproof fastener comprises at least one of: a zipper, an autosealing pair of rubber bands, or a hook and loop fastener, commonly referred to as a Velcro™ fastener.

According to an embodiment, there is further provided a proximal band and a distal band to be provided around the body member at a proximal end and a distal end of the sleeve body, respectively, each of the proximal band and the distal band comprises an inner antiskid surface to press against the body member and remain thereon.

According to an embodiment, each of the proximal band and the distal band is inflatable to press against the body member and provide waterproofness to the proximal end and to the distal end of the sleeve body.

According to an embodiment, there is further provided a cutout pocket provided inside the openable window for receiving the catheter when the protective cover is worn by the patient.

According to an embodiment, the protective cover is free of any rigid member covering the body member.

According to another embodiment, the sleeve body and the openable window comprise an elastic fabric, further comprising an over-sleeve which is a waterproof tube to provided in a kit with the protective cover and to be extended around the protective cover to protect the protective cover from water.

According to another aspect of the invention, there is provided protective cover for a body member of a patient having a catheter inserted therein at a catheter insertion point, the protective cover comprising a sleeve to wrap around the body part over the catheter, the sleeve comprising:

a sleeve body covering a substantial surface of the body member of the patient, the sleeve body being made of a material that is non-rigid and flexible, the sleeve body conforming to the surface of the body member of the patient that is covered;

a joint-covering portion for covering a joint of the body member and made of an elastic material; and an openable window for covering and providing access to the catheter when the protective cover is worn, the openable window being openable with respect to the sleeve body and the joint-covering portion, the openable window defining an inner surface and comprising an area on the inner surface for securing an antiseptic agent, wherein the inner surface of the openable window is applied onto the catheter insertion point when the openable window is closed, wherein the inner surface is brought away from the catheter insertion point when the openable window is opened, the sleeve body acting as an intermediate portion joining the joint-covering portion and the openable window in a watertight fashion when the openable window is closed, wherein the protective cover is free of any rigid member covering the body member.

According to an embodiment, there are further provided antiskid bands at a first end and a second end of the sleeve for attaching the protective member to the body member.

According to an embodiment, there is further provided a cutout pocket provided in the fabric for receiving the catheter when the protective cover is worn by the patient.

According to an embodiment, the protective cover is free of any rigid member covering the body member.

As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which:

FIGS. 2A-2M are perspective views and pictures of a protective cover, according to an embodiment of the invention;

FIGS. 4A to 4C are schematic views illustrating an example of a venous catheter protector wrapped around the patient's arm, in accordance with an embodiment;

It will be noted that throughout the appended drawings, like features are identified by like reference numerals.

DETAILED DESCRIPTION

Figure 1:
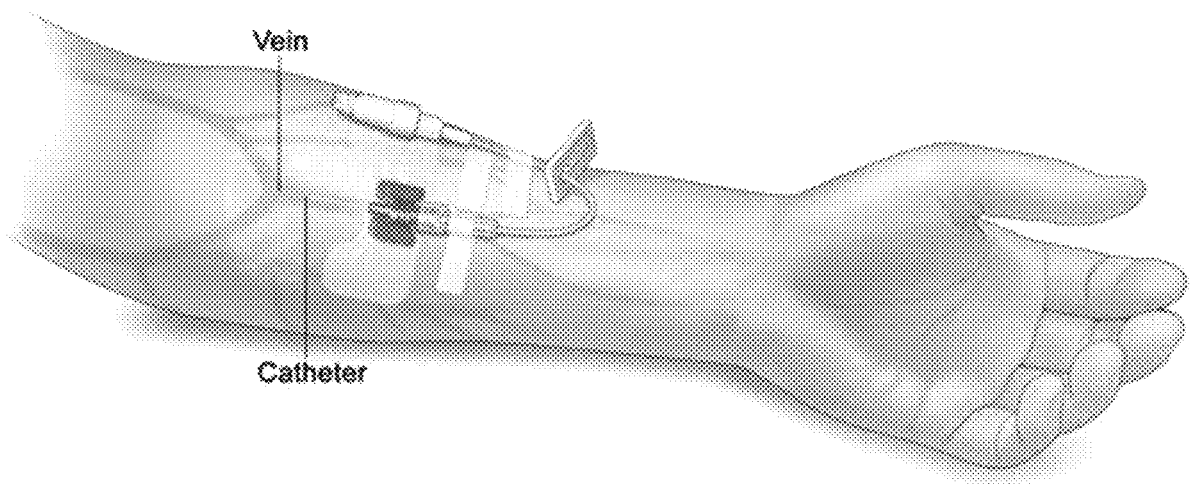
FIG. 1 is a picture illustrating an example of a conventional catheter installed on the arm of the patient.

The embodiments describe a protective cover for venous catheters. The protective cover, or protector 100, described herein below can also be used to cover an already existing local protector for the catheter. Local protectors for catheter sites (not to be confused with the protector 100) can be installed in hospitals, but such local protectors are not suited for everyday life. Local protectors offer good protection of the catheter site itself and are therefore useful for maintaining the catheter site in a good state to avoid infections. However, this local protector is installed in a nursing context, and its purpose is only to contribute to the healthy state of the patient with respect to the catheter site. Outside of a nursing environment, the local protector shows its limits as it is not well adapted to everyday life. The local protector, is usually bulky or has an inconvenient shape and does not provide features or advantages such as: facility to get dressed up with the local protector installed, discretion of the catheter or the local protector (e.g., plaster) covering it, protection against patients with confusion (delirium, dementia or mental disabilities) that would be free to manipulate and remove the local protector, The protective cover, or protector 100, described herein below protects both the catheter site and the local nursing protector already installed thereon. It provides discretion and privacy, as the overall appearance does not attract the eyes of other people. It allows the person to dress up easily despite the presence of the catheter and of a local protector thereon, since the overall result is a smooth and relatively tight surface (thanks to the use of flexible materials to fit or adapt to the shape of the body member) over which clothing can be put on. It also protects the catheter site and the local protector from being hit or displaced involuntarily, from being removed accidentally or being manipulated by people with confusion (delirium, dementia or mental disabilities) who do not understand why they have a local catheter protector on their body. If no local protector is being worn, the protector 100 still offers the advantages with regard to the catheter that would otherwise be exposed.

The cover is configured to protect its user from exposure to bacteria, humidity, dust, water and other contaminants. According to an embodiment, it can provide some sort of visual indicator of the changes in temperature and the levels of these contaminants around the area being protected. The cover may be provided in the form of a sleeve for the arm or a relatively tight wrap for other areas of the body. The present invention will be more readily understood by referring to the following examples which are given to illustrate the invention rather than to limit its scope.

Now referring to an embodiment shown in FIGS. 2A-2M and 3A-3F, the catheter protector 100 is a sleeve covering an elongated member of the body (e.g., human body, or body of an animal). For example, it can be a sleeve covering the arm of a person wearing it. The sleeve can have a generally tubular shape, covering the surface all around the body member over a length thereof, and is preferably made of an elastic material to press against the skin and wrap around the body member.

Figure 2A:
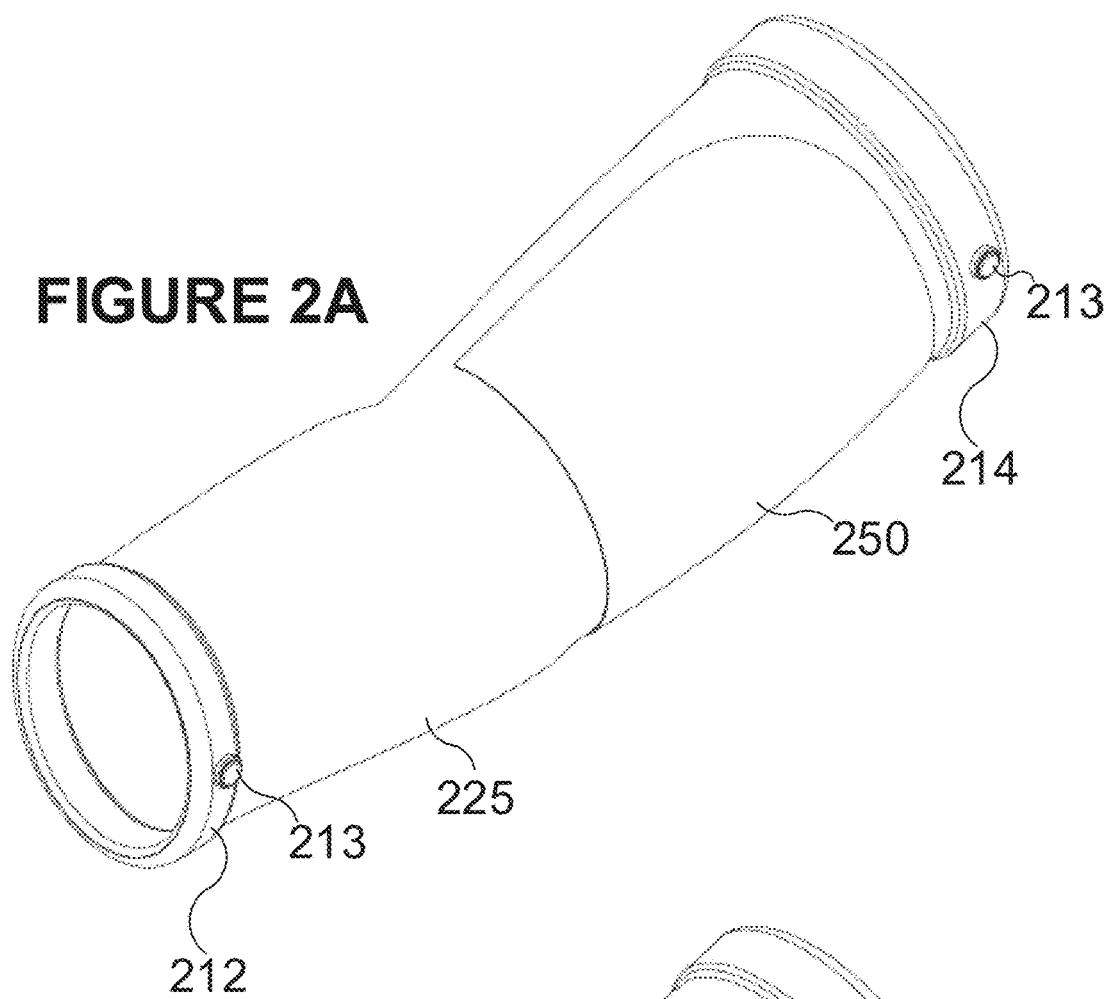
Figure 2B:
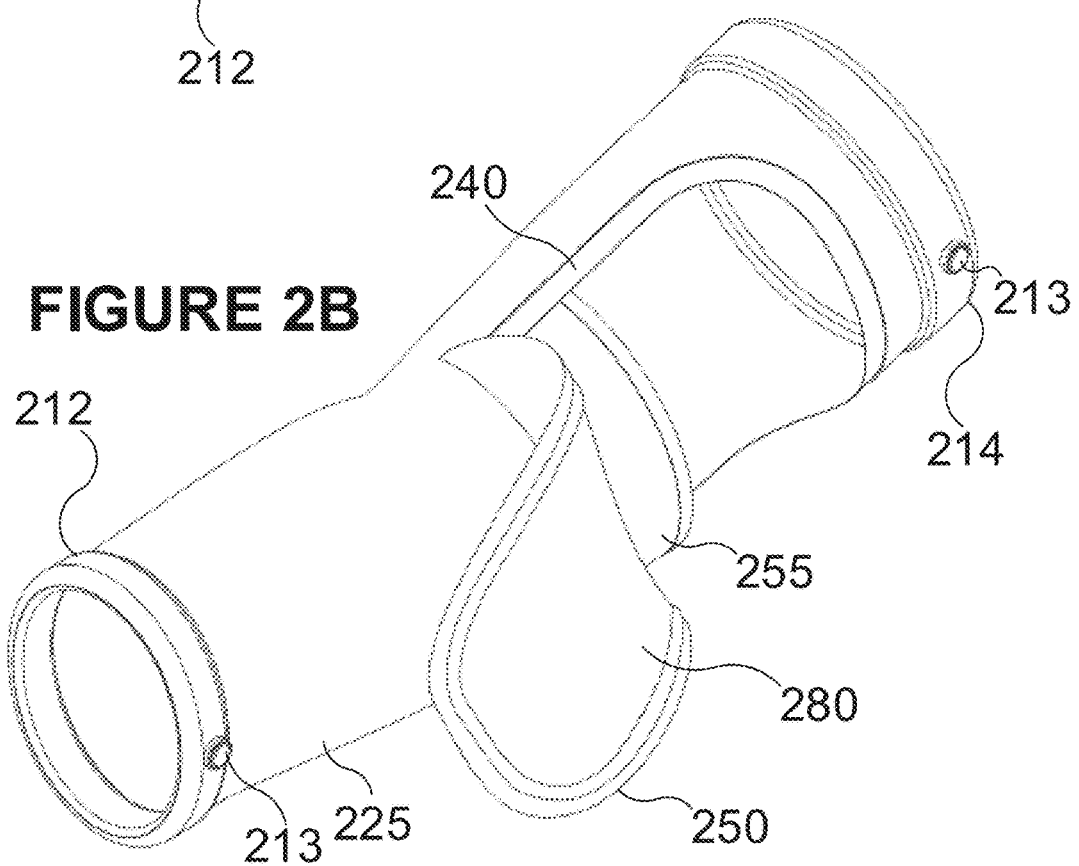
Figure 2C:
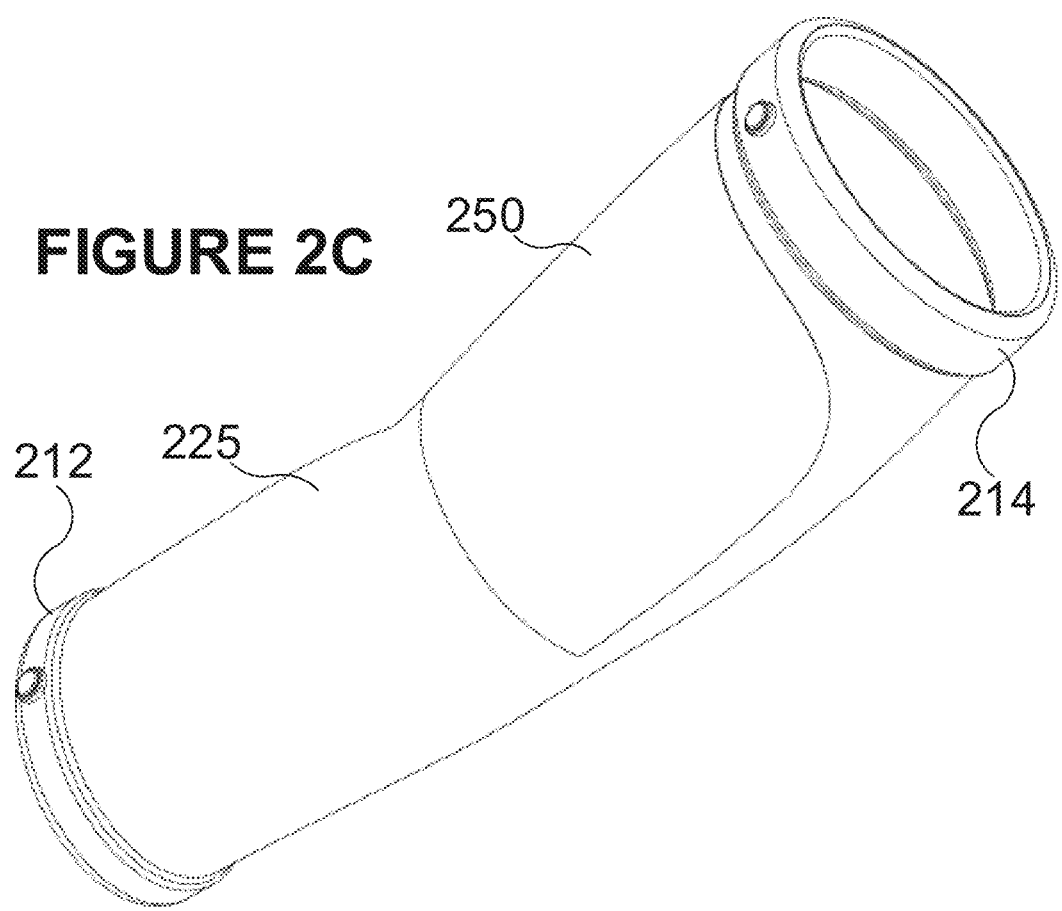
Figure 2D:
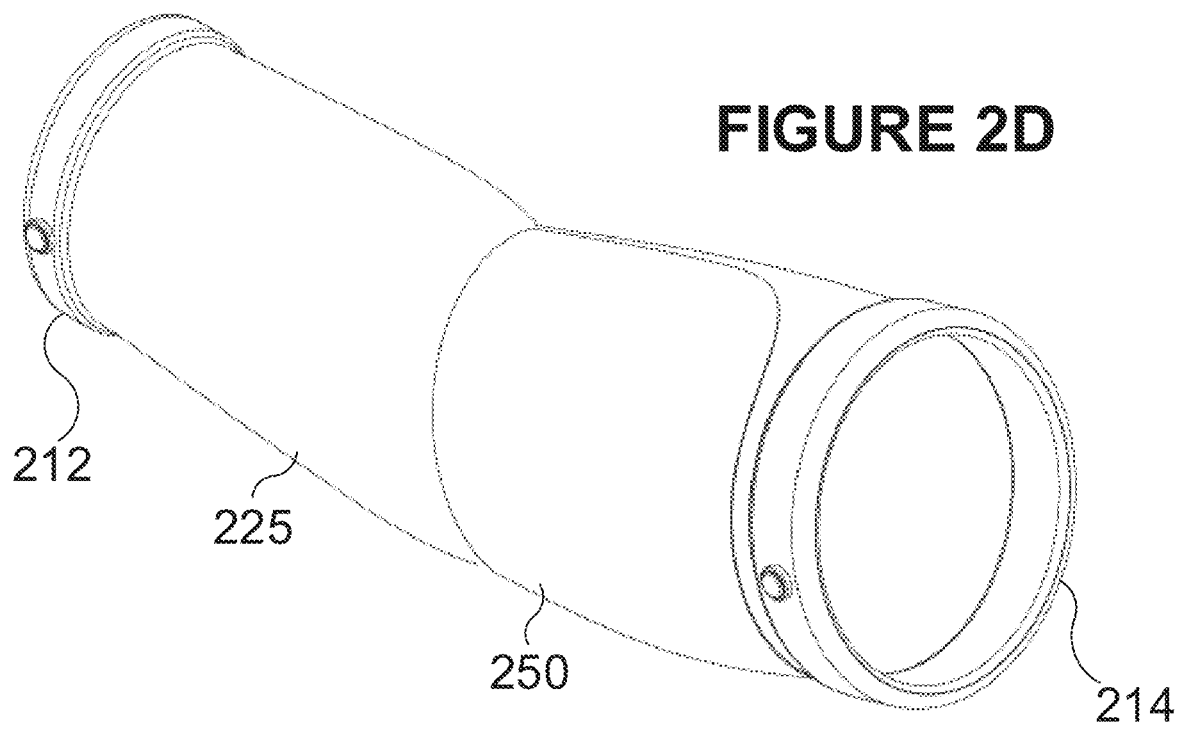
Figure 2J:
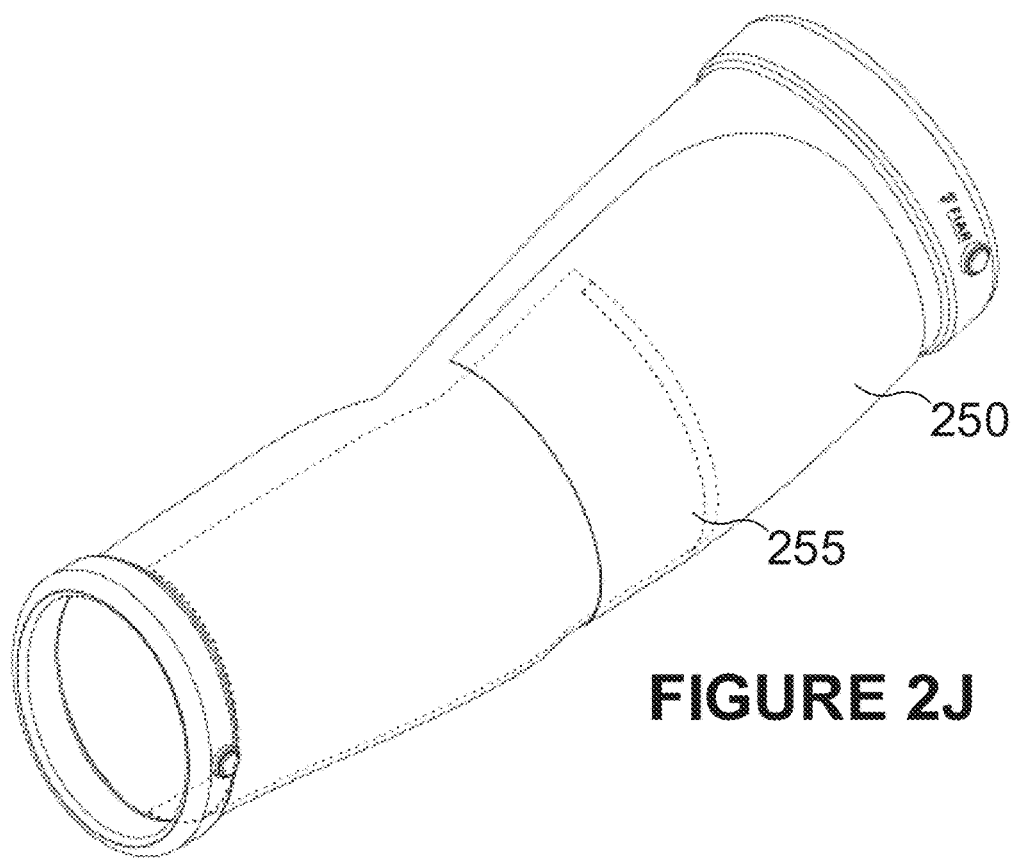
Figure 2K:
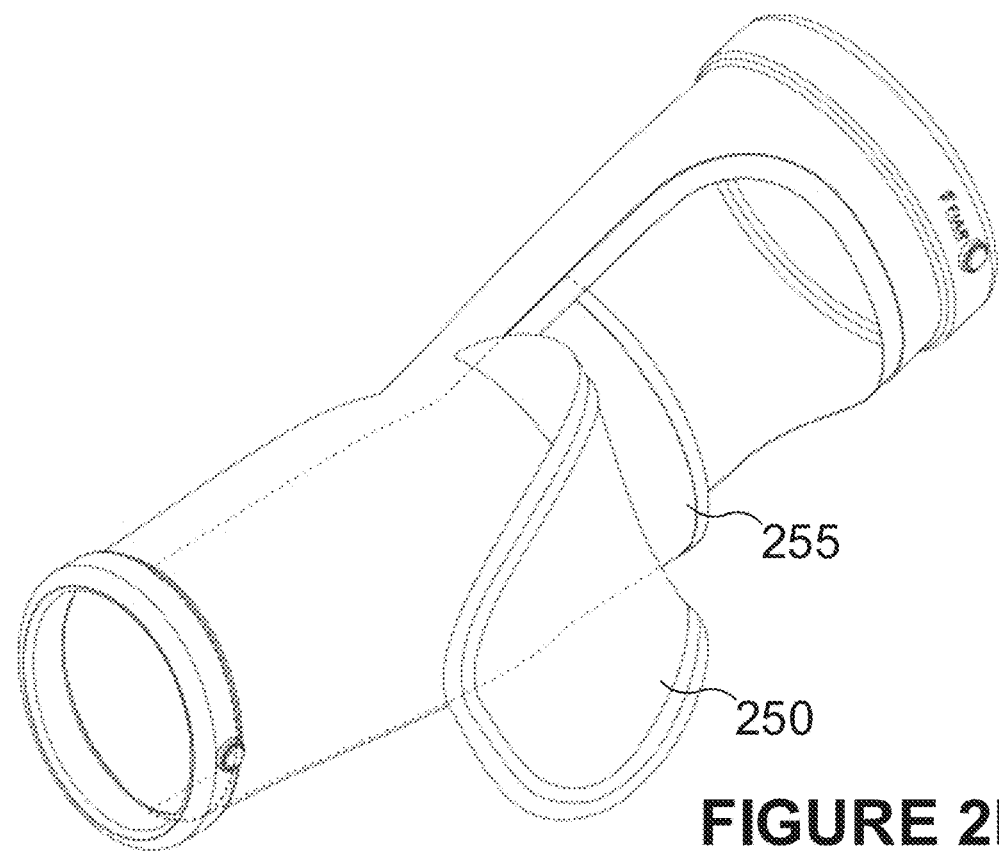
Figure 2L:
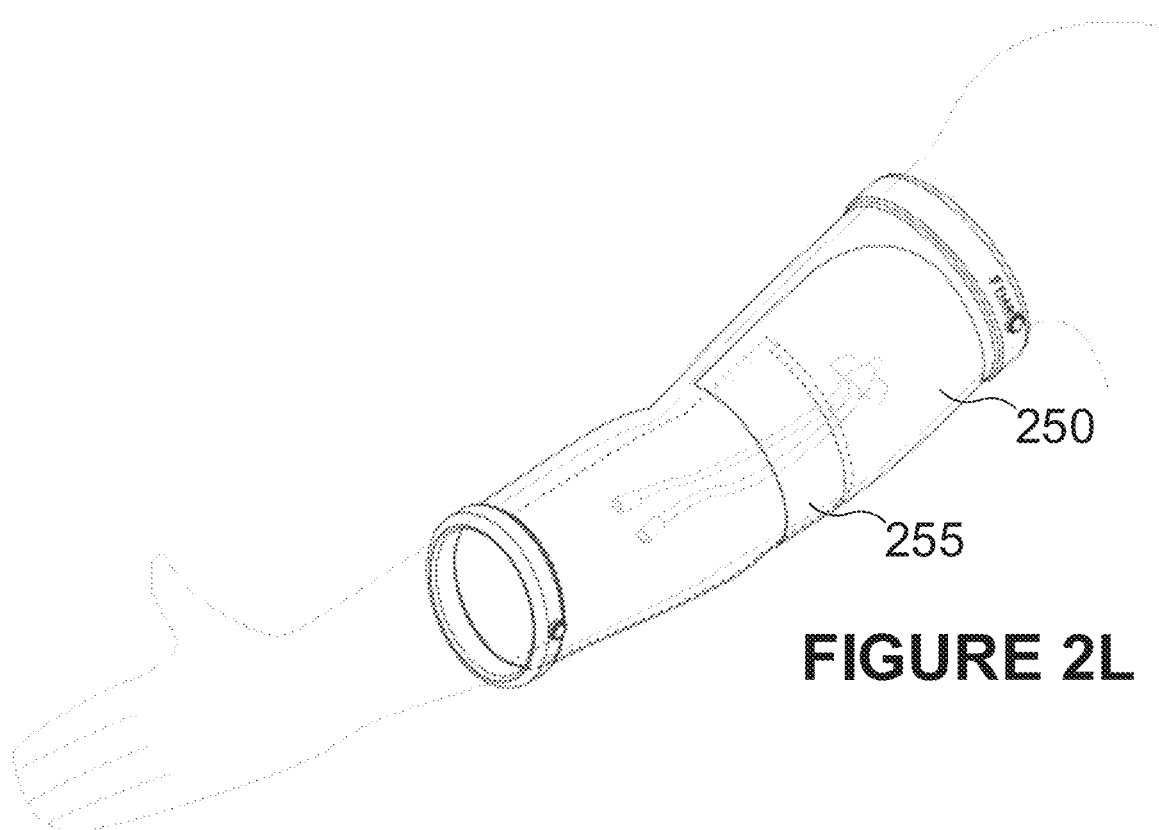
Figure 2M:
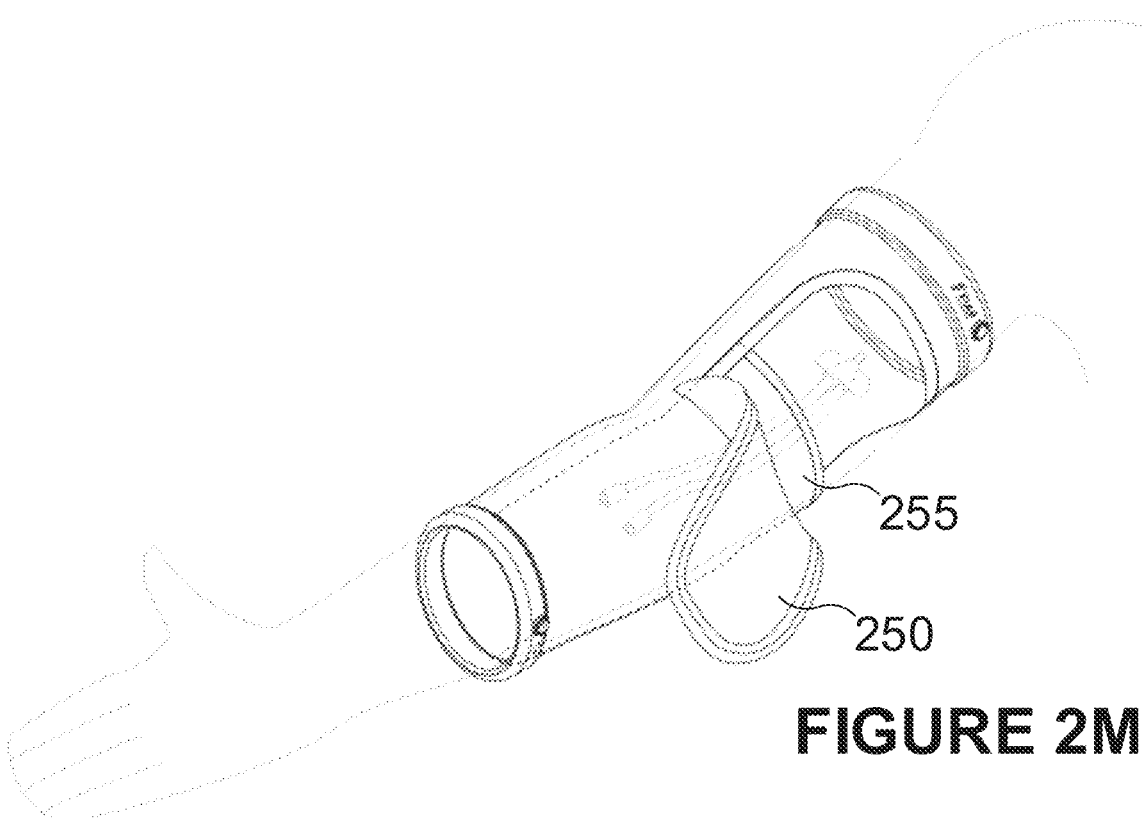
Figure 3A:
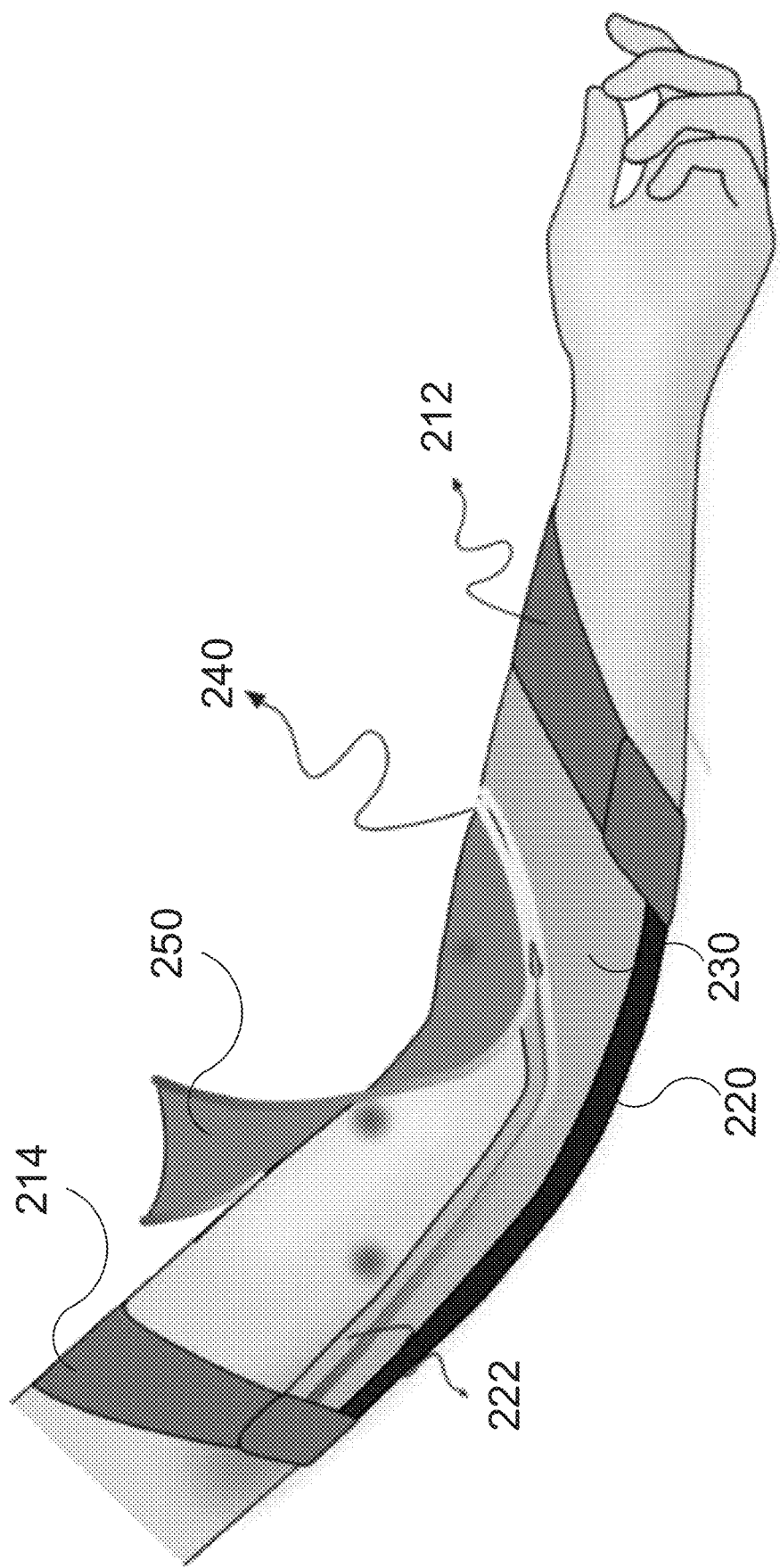
FIGS. 3A-3F are perspective views and pictures of a protective cover in accordance with another embodiment of the invention.
Figure 3B:
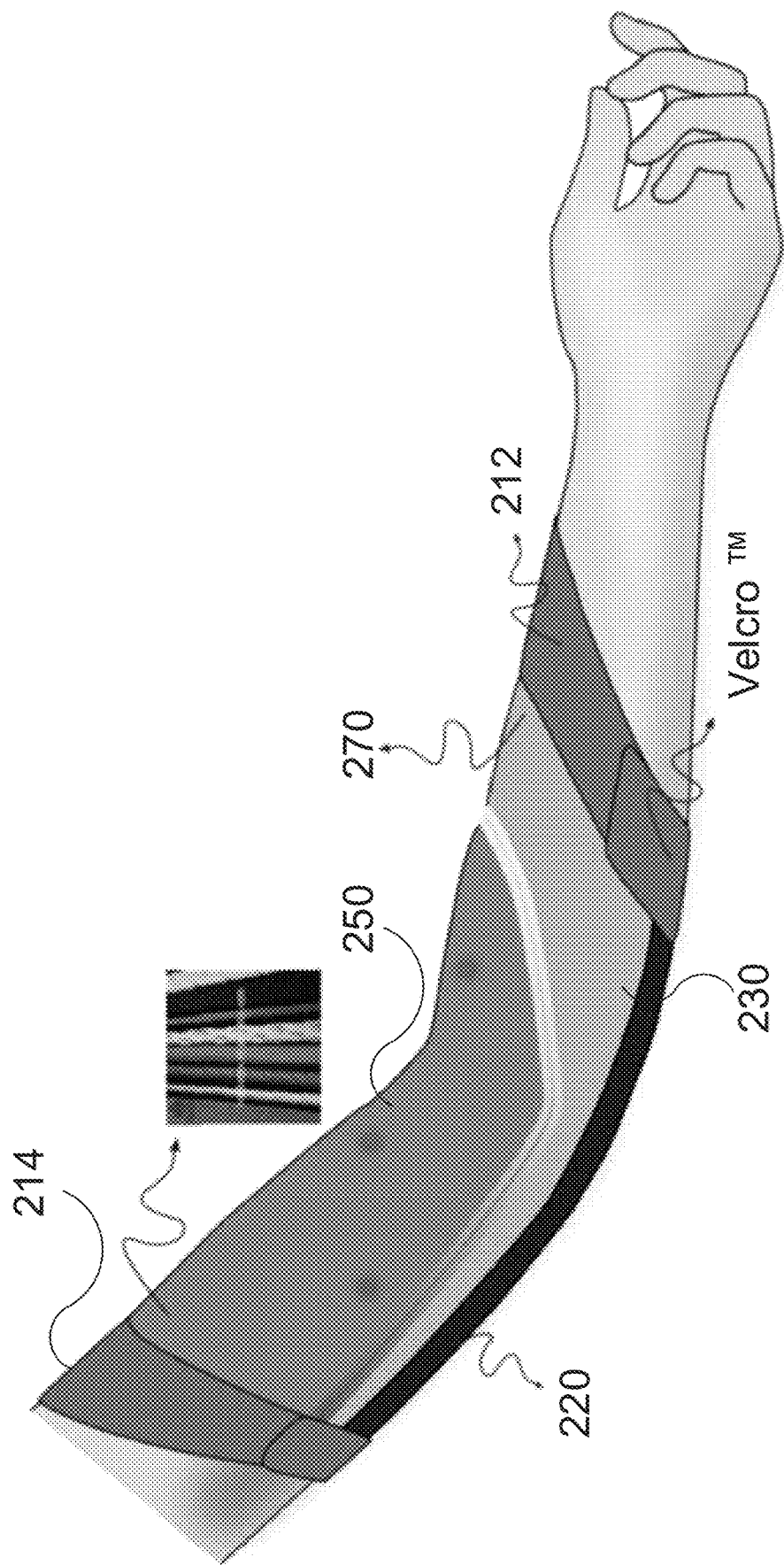
Figure 3C:
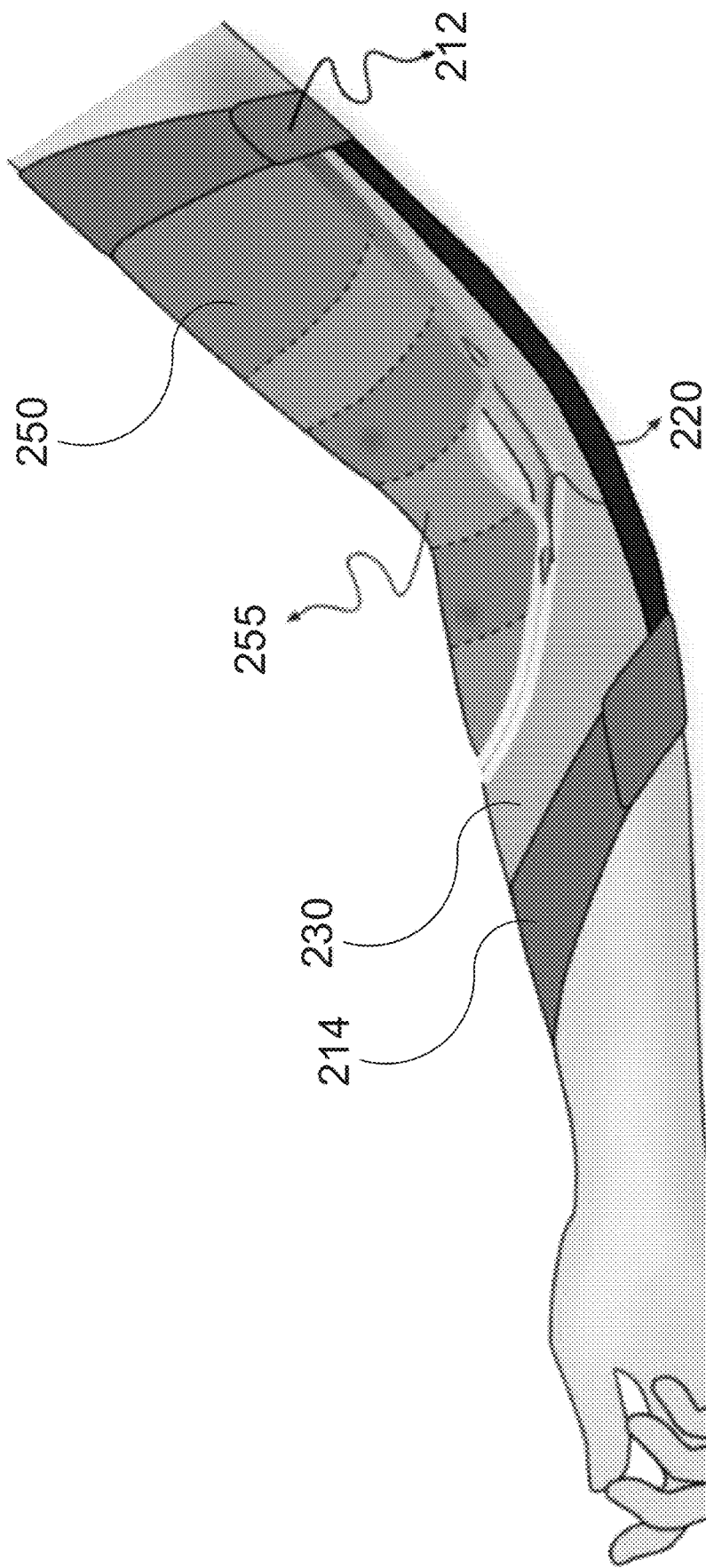
Figure 3D:
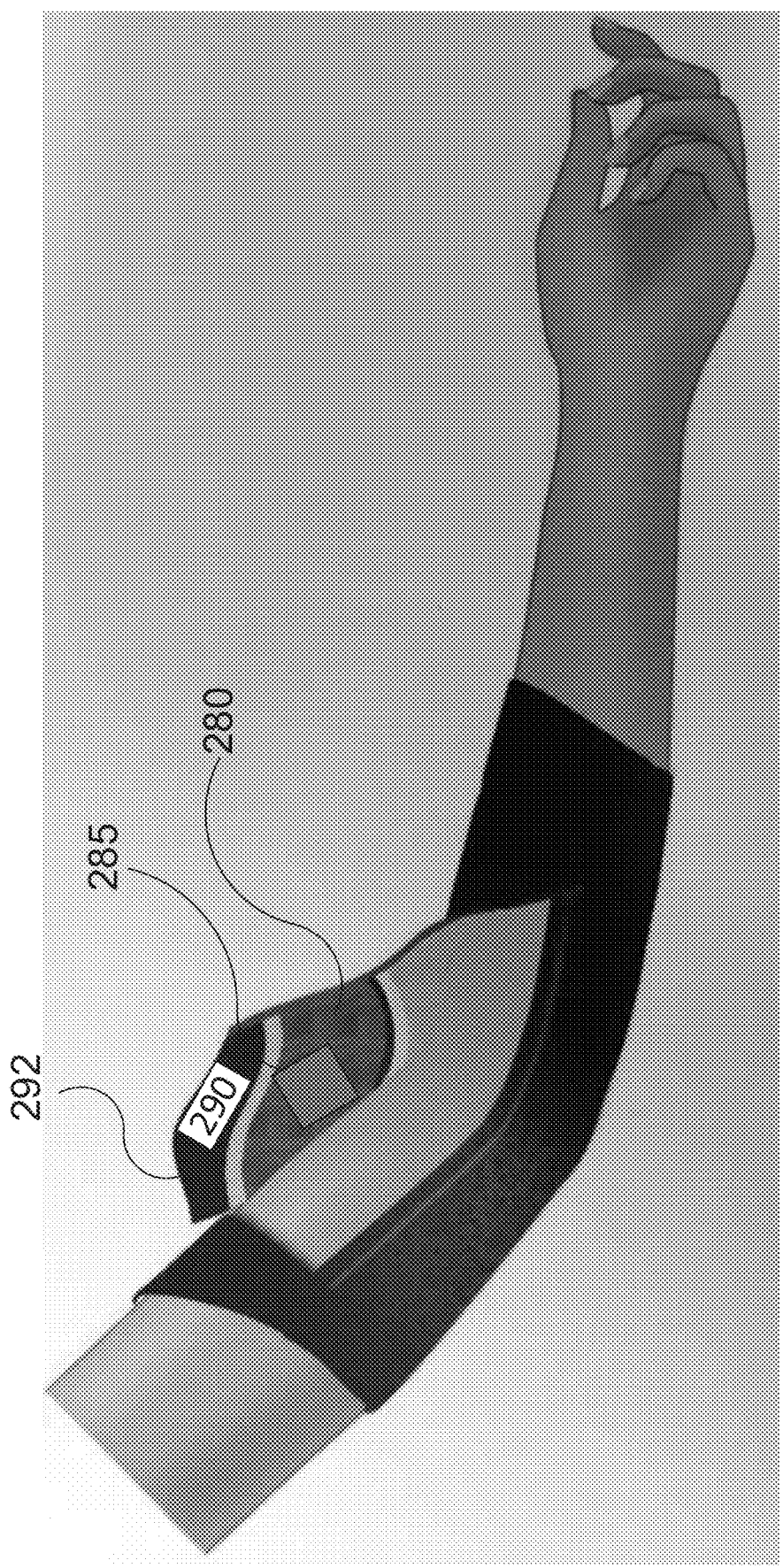
Figure 3E:
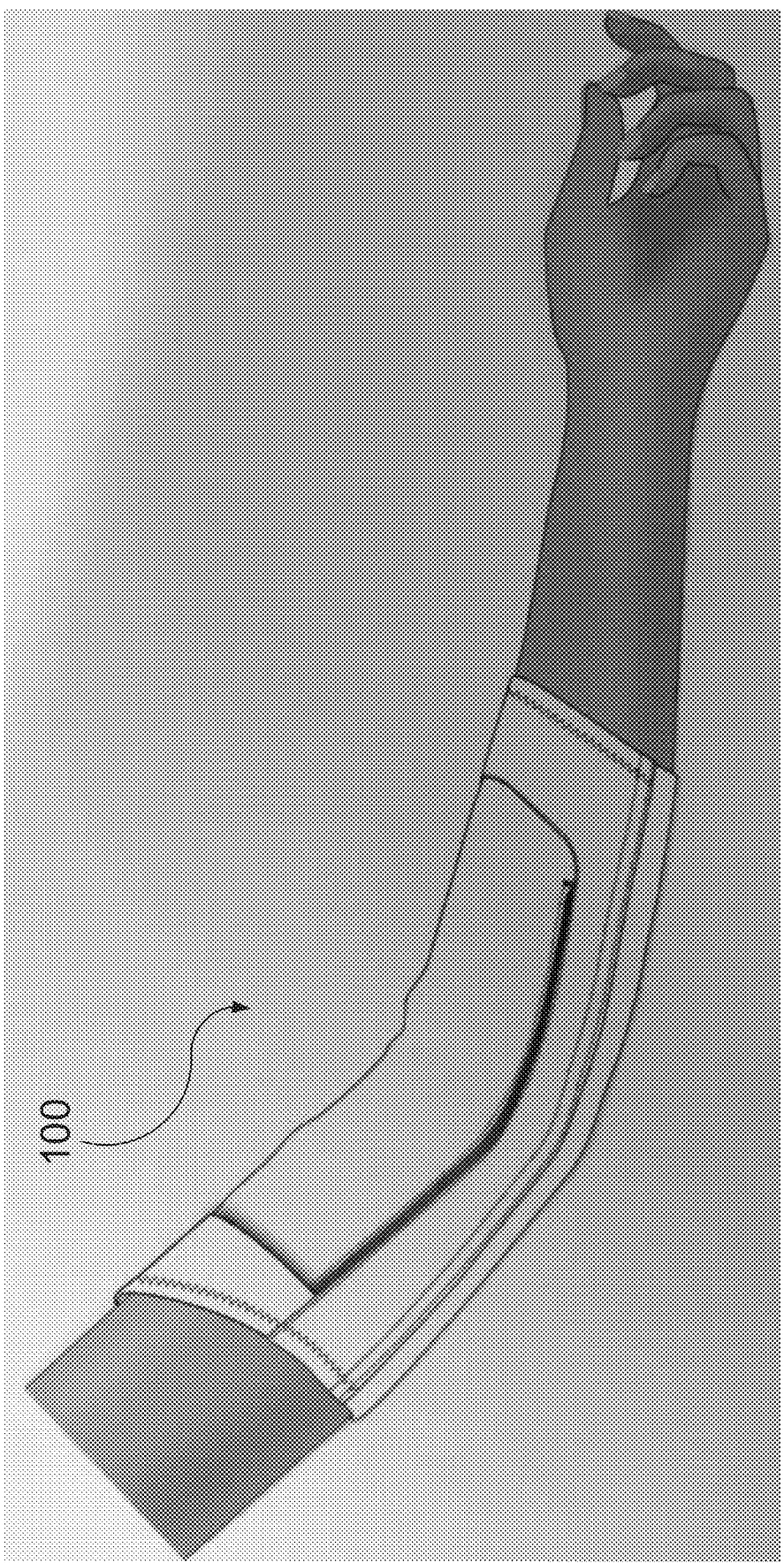
Figure 3F:
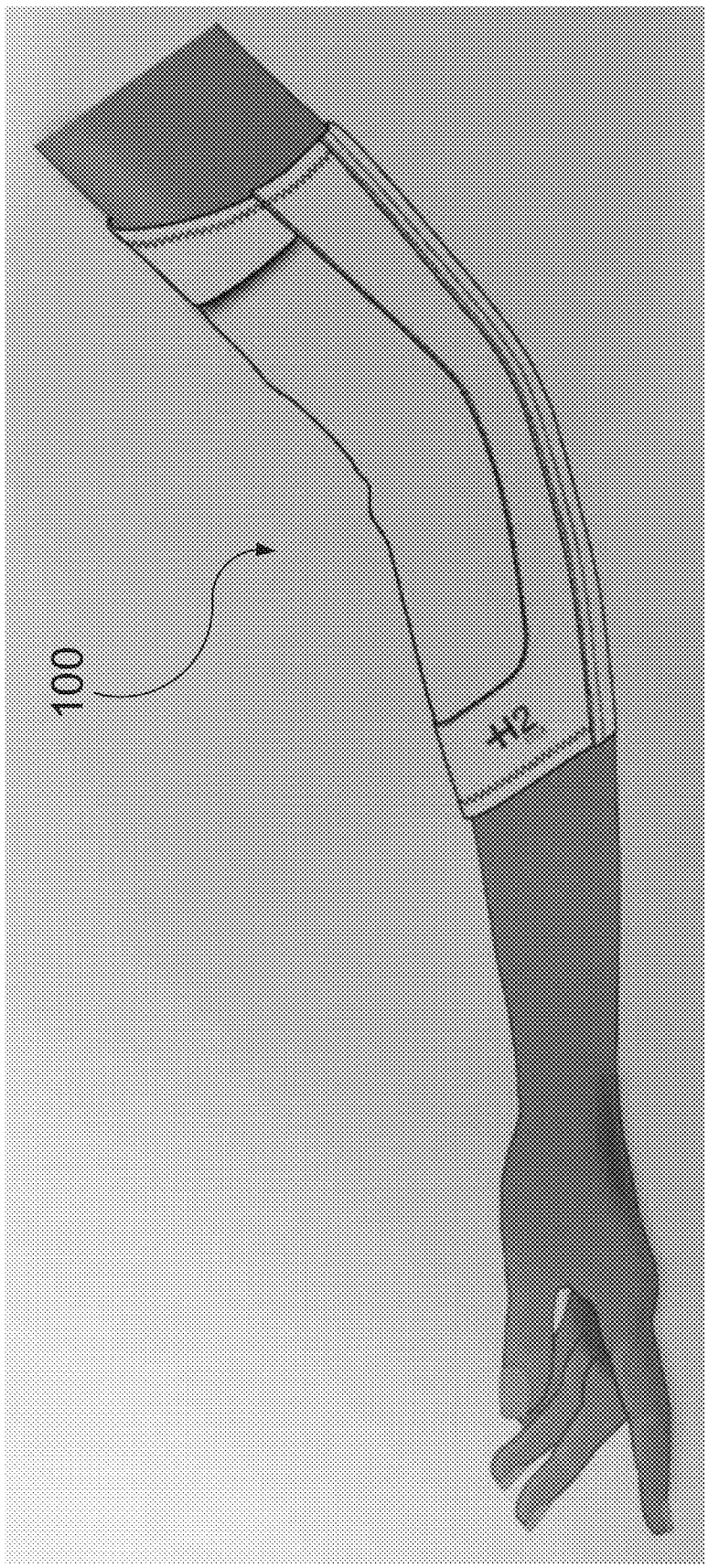

According to a more particular embodiment, the sleeve can be made of a plurality of sections which together form the generally tubular shape of a sleeve. As shown in FIGS. 2A-2M and 3A-3B, the sleeve can comprise an antiskid section, or even two of them. The antiskid section allows the sleeve to remain in place on the body member and not slide thereon. The antiskid section may be provided as a band (212, 214) and may comprise a non-sliding material such as silicone on the inner surface of the band (212, 214) in contact with the skin to provide the antiskid feature. The band may be made of an elastic material to fit with different member sizes. For greater comfort, the band (212, 214) may also have an adjustable length or tension, for example by providing an adjustable fastener, such as a hook and loop fastener, commonly referred to as a Velcro®™ type attachment that allows to vary the length of the band (212, 214) and thus remain on a selected part of the body member. According to an embodiment, there is an antiskid band at the two ends of the sleeve, i.e., bands 212 and 214, as shown in FIGS. 3A-3B. As the arm usually extends in a longitudinal axis, the band (212, 214) would be expected to surround the member in a plane perpendicular to this longitudinal axis. However, it may extend in a plane forming an angle with this normal. This inclination can help maintaining the sleeve at the right position along the biceps and triceps of the arm since it extends along the edge of the protuberance of these muscles. Therefore, providing the band in the form of a circular ring having a normal axis inclined (angle≠0) from the longitudinal axis of the member (e.g., arm) ensures that the band is supported along the line of the muscle of this body member, ensuring proper maintenance of the whole sleeve in its position. This configuration ensures that the sleeve may be used for a variety of actions in which the sleeve would otherwise move. The person wearing the sleeve may thus engage in sport activities and perform various types of everyday activities involving different movements without being bothered by the catheter as it is protected by the well-maintained sleeve, or without risking displacing the catheter.

The embodiment shown in FIGS. 2A-2M comprises a sleeve body 225, which is the main portion of fabric that covers the surface of the body member having the catheter insertion point being protected. The sleeve body 225 should cover the surface of the body member uninterruptedly between the two bands 212, 214, with the only exception being the openable window 250. Together, they cover the surface of the body member uninterruptedly without any exception, thus providing total coverage and thus protection from water and other liquids, and/or protection from debris of various types.

The alternative embodiment shown in FIG. 3A-3F further shows that the remaining parts of the sleeve can be divided in two portions of different purposes, namely the elbow-covering member 220 and the U-shaped non-extensible portion 230. In this particular embodiment, an elbow-covering member 220 is made of an elastic material (e.g., neoprene or other material with similar properties) to provide flexibility and elasticity about the outer portion of the arm where the elbow is located. The elbow-covering member 220 may cover a joint other than an elbow, and should be elastic to withstand and adapt to the movements of the joint being covered. This elbow-covering member 220 is restricted to the outer surface of the arm. The elbow-covering member 220 can also be flexible but not particularly elastic, as described above. On the inner surface of the arm, there is provided a U-shaped non-extensible portion 230 made of a non-extensible fabric which is attached to both bands (212, 214) at its ends and to the elbow-covering member 220 along its edges for providing stability and holding the parts together. An openable window 250 is provided to cover the remaining portion where the catheter is expected to be located, thereby closing the tubular shape of the sleeve. This openable window 250 is fastened in a releasable fashion on at least a portion thereof to the U-shaped non-extensible portion 230 and can thus be opened or closed to access the catheter.

An example of appropriate means for fastening the waterproof fastener can include: a zipper, an autosealing pair of rubber bands, or a hook and loop fastener, commonly referred to as a Velcro™ fastener. While the zipper provides a secure fastening, the autosealing pair of rubber bands (e.g., two silicone bands that can be brought together and thereby stick together) can be preferred for its simplicity and especially because it does not give rigidity to the sleeve. The waterproof fastener 240 should be waterproof to allow the person to take a shower. The U-shaped non-extensible portion 230 or the sleeve body 225 can advantageously comprise an edge 232 that extends from the main surface of that portion 230 under the waterproof fastener 240 to protect the skin of the patient (or its body hair or the catheter) from being zipped or adhered to when the openable window 250 is being opened or closed. According to an embodiment, the waterproof fastener 240 can include an overlapping band of fabric, as shown in FIG. 2B. According to a more specific embodiment, the overlapping band of fabric of the waterproof fastener 240 may include a self-adhesive coating such as the pair of rubber bands discussed above, or other adhesive coating that is reusable.

The openable window 250 can be advantageously made with textured neoprene to act as a cushion for protecting the catheter entry site. Additional inside-facing bands can be provided inside the openable window 250 to prevent the catheter to rub on the skin.

The sleeve body 225 (FIGS. 2A-2M) or the elbow-covering member 220 and the U-shaped non-extensible portion 230 (FIGS. 3A-3F) need to be waterproof to avoid water infiltration inside the cover and presence of moisture in addition to that already produced by the body. According to an embodiment, the fabric that makes up these portions of the cover is waterproof but breathable or perspirable material (i.e., that allows water vapor therethrough) that allows the skin to breathe and send out the moisture and sweat produced by the skin. An example of a suitable material may include polytetrafluoroethylene fabric, commonly referred to as Goretex™® fabric. Every material needs to be flexible (which is normally a natural property of a fabric, which is the contemplated material for the cover), and not rigid (e.g., any hard plastic, bulk metal or other hard and substantially underformable materials), to adapt to the varying shape of the body member. Indeed, the shape of the body member is normally irregular and changes over time as the body member is being moved (e.g., an arm is not a perfect cylinder and can move, especially about the elbow). If the cover comprises the U-shaped non-extensible portion 230, this portion does not need to be elastic. However, the sleeve body 225 (FIGS. 2A-2M) or the elbow-covering member 220 (FIGS. 3A-3F) need to be made of an flexible fabric, and preferably not particularly elastic, as this would prevent waterproofness, although a small degree of elasticity can be expected such that the fabric can stretch slightly, preferably by using a bidirectional stretchable material (i.e., in both directions along the surface of the fabric). An example of such a material that offers good waterproofness and a small elasticity is a 3-ply laminated polyester.

Other preferable properties of the fabric may include: mechanical resistance to tear or friction, wind blocking, shape memory, light weight, washable and fast drying material, and UV protection. It should also be at least bacteriostatic to avoid bacterial growth and complement the antiseptic agent to be provided against the catheter insertion point.

The join between each portion preferably comprises a waterproof seal portion 270 at the edge of each portion, as described above with respect to a first embodiment, to prevent infiltration of water and other contaminants to the catheter area. The waterproof seal portions 270 may be elastic to press against the skin in a watertight manner.

A cutout/pocket 255 as described above may be also provided within the protective cover 100, and preferably in the openable window 250, to house the catheter, as described above with respect to a first embodiment, and as well shown in FIGS. 2J-2M. A pocket cover may be provided for the pocket 255 for covering the catheter area in a waterproof manner. The pocket cover provides visual and physical access to the catheter area. Padding may also be provided there since this part of the protective cover 100 will be provided against the skin and will receive catheter-related equipment such as tubing; the padding on both sides of the cutout pocket can reduce irritation.

According to an embodiment, there is provided an area 292, preferably inside the protector 100, and preferably on an inner surface of the openable window 250, where a label 290 can be installed. The label 290 is preferably self-adhesive (i.e., it is a sticker) to avoid requiring further securing means. Alternatively, a transparent window (e.g., a fabric mesh) can be used to insert a non-adhesive label therein. The label 290 can include information on the patient, such as identity or health problems (allergies, diabetes, etc.), and/or can comprise instructions pertaining to the maintenance of the protector or to the care to give to the patient relative to the catheter, or information about the treatment (e.g., last time or date of treatment).

According to an embodiment, there is provided an area 280 inside the protector 100, and preferably in the openable window 250, in which an antiseptic agent 285 can be provided to prevent infections within the area covered by the protector. According to an embodiment, the area 280 can be made to receive an antiseptic solution, gel or viscous liquid that can be reapplied when necessary. According to another embodiment, the area 280 can be a pocket in which a pad can be inserted, the pad being impregnated with the antiseptic agent. The pocket can also be used to insert a relatively solid substance having antiseptic properties, such as a pad impregnated with an antibacterial agent as commonly used in a nursing environment. This substance can also be a natural substance, such as a substance of a vegetal source having such properties, such as essential oils or vegetal extracts. According to another embodiment, the area 280 can be lined with a lining or coating of an antiseptic substance, e.g., a silver lining.

According to an embodiment, the bands 212, 214 can be inflatable, as shown in FIGS. 2A-2M (however, the inflatable bands can also be provided on other embodiments than those of FIGS. 2A-2M, such as the two-part sleeve body embodiment of FIGS. 3A-3F). An inflation port 213 can be provided on each of the inflatable bands. The inflation port 213 allows inserting a tool for inflating the band, and further allows deflating the band, e.g., by unplugging the inflation port or by pressing thereon (to free the gas stored in the inflated band), depending on the exact implementation. The inflation port 213 can further comprise a port for inflating and another for deflating. Inflation is particularly well adaptable to the size of the body member, thus providing greater customization of the protective cover 100 in terms of sizing. Moreover, a proper inflation ensures that the bands 212 and 214 are not only antiskid, by also very watertight as they press on the body member all around it. Providing the band as an inflatable band makes it more comfortable and watertight, thus keeping the cover 100 waterproof with a greater level of confidence.

The cover 100 may have an aesthetically appealing and sporty looking exterior that allows the patient to go out in public and practice their day to day activities without embarrassment and without drawing the stares of people around them, while at the same time being protected from water, dirt, sun, and other contaminants that infect the catheter area or that diminish the protection provided by a local catheter protector.

According to an embodiment, padding can be added inside the cover on specific sites, especially at the border between different portions of the cover, to make the inside of the cover more comfortable and avoid friction of seams with the skin.

According to an embodiment, there can be added a rigid orthotics device inside the protective cover 100 (not belonging to the protective cover 100 since the protective cover 100 itself is free of any rigid member). The rigid orthotics device is an elongated, solid material that supports the body member and prevent movement, such as the hinge movement by the elbow. The rigid orthotics device may be useful for some medical reason, and the protective cover 100 (free of any rigid member) can adapt to its presence as it is flexible and elastic and its shape can adapt to the presence of that rigid orthotics device along the body member.

Now referring to another embodiment shown in FIGS. 4A to 4C there is shown an example of a venous catheter protector wrapped around the patient's arm, in accordance with an embodiment. As shown in FIG. 4A, the protector 100 includes a main portion 102 that wraps around the body part e.g. hand, chest, leg, or the like as exemplified in FIGS. 4A to 4C. FIG. 4A shows the cover on one side and FIGS. 4B and 4C show the cover on from the opposite side. The wrapping portion 102 may include a first end and a second end 104 which are configured to releasably attach to each other and provide some flexibility to accommodate body parts of different dimensions. A non-limiting example of such ends includes a hook and loop fastener, commonly referred to as a Velcro®™ fastener. For example, as shown in FIG. 4A the end portions 104 are attached to each other and may detached by pulling them following the arrows 106.

The wrapping portion 102 may include waterproof seal portions 108 provided on each side of the catheter area and preferably at the edge of the wrapping portion 102 as exemplified in FIGS. 4A to 4C to prevent infiltration of water and other contaminants to the catheter area. The seal portion 108 may be elastic to press against the skin in a watertight manner.

A cutout/pocket 110 may be provided within the wrapping portion of the cover 100 to house the catheter 112 as shown in FIG. 4C. A pocket cover 114 may be provided for the pocket as exemplified in FIG. 4B for covering the catheter area 110 in a waterproof manner. The pocket cover 114 provides visual and physical access to the catheter area as exemplified in FIG. 4C.

Figure 5A:
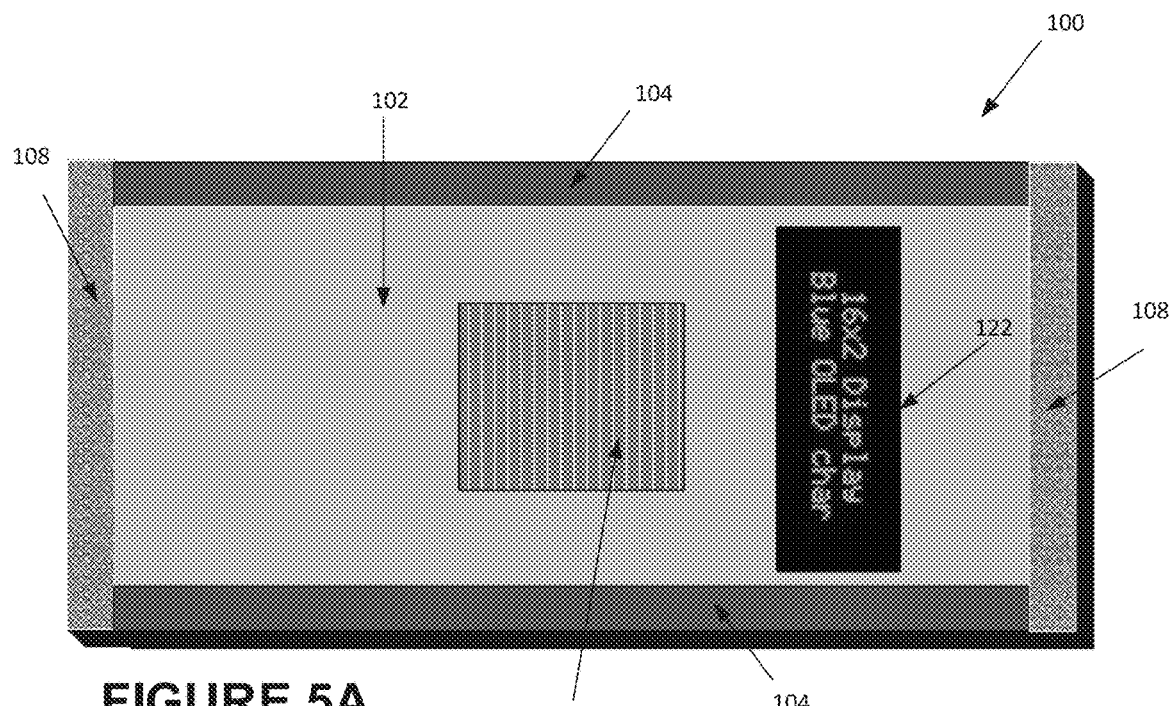
FIG. 5A is a top view of an exemplary venous catheter protector with the pocket cover, in accordance with an embodiment.
Figure 5B:
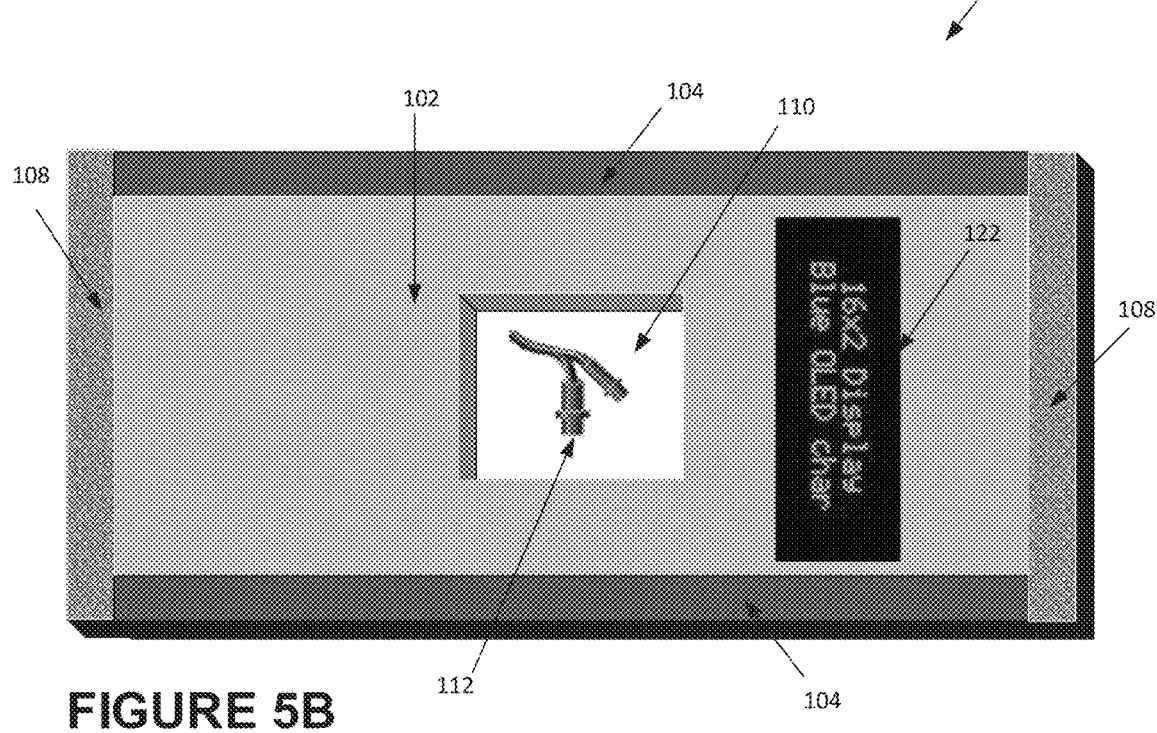
FIG. 5B is a top view of an exemplary venous catheter protector without the pocket cover, in accordance with an embodiment.

FIG. 5A is a top view of an exemplary venous catheter protector in accordance with an embodiment with the pocket cover and FIG. 5B is a top view of an exemplary venous catheter protector in accordance with an embodiment without the pocket cover. As discussed above, the cover 100 wraps around the body member (e.g. hand) whereby portions 104 detachably attach to each other and seal portions 108 provide a tight waterproof connection with the skin to prevent infiltration of water and contaminants to the catheter area in the pocket 110.

The protective cover in accordance with an embodiment includes a smart fabric layer that comes in contact with the skin and allows for collecting data about the condition of the skin surrounding the catheter. The fabric may include a variety of sensors such as temperature sensors, humidity sensors, and sensors adapted to detect other parameters such as acidity, salt, fungus, bacteria, and other contaminants that may infect or contaminate the opening receiving the catheter and/or the blood.

Figure 6:
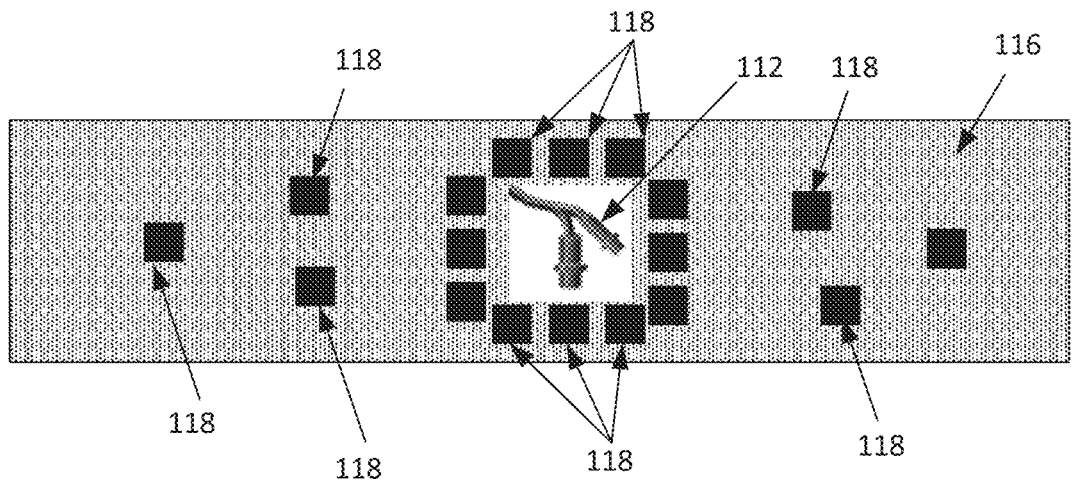
FIG. 6 is a top view of an exemplary smart fabric layer showing different sensors provided around the catheter to collect data about the catheter area.

FIG. 6 is a top view of an exemplary smart fabric layer showing different sensors 118 provided around the catheter 112 to collect data about the catheter area. In an embodiment, the sensors may be configured to surround the catheter area to detect presence of sweat, humidity, perspiration infiltrating from any side toward the catheter, as exemplified in FIG. 6.

Figure 7:
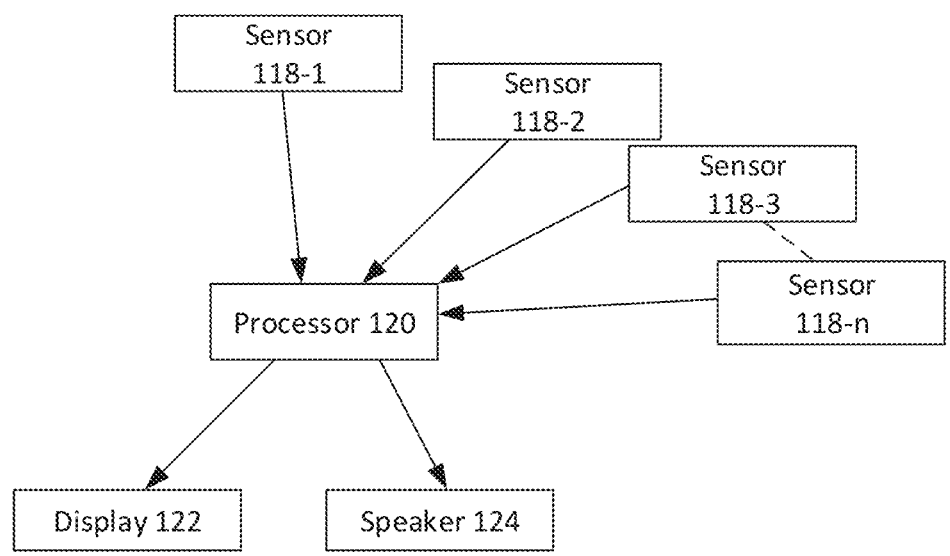
FIG. 7 is a block diagram of a monitoring system provided in the protective cover for monitoring the catheter area.

FIG. 7 is a block diagram of a monitoring system provided in the protective cover for monitoring the catheter area.

As shown in FIG. 7, the sensors 118 may be operatively connected to a processor 120 e.g. microprocessor for processing the data collected by the sensors 118. The processor 120 may be connected to a visual display 122 for displaying visual messages and may also be connected to a speaker 124 for producing voice messages or tones based on the data received from the different sensors. The type of alerts and messages may be selected by the processor based on the type of contaminant and the quantity thereof.

The visual messages may take different forms and could range from a simple change of color to a written message. For example, the processor 120 may display a green light on the display 122 to indicate that the patient can continue with their activity, or a yellow light to indicate that a cleaning is required soon, or a red light indicating that immediate attention is required. A written message may also be displayed indicating the type of action that need to be taken e.g. immediate cleaning required, or contact emergency room etc.

Audible messages emitted by the speaker 124 may also range from a simple tone to a pre-recorded voice message such as "visit emergency room", or "water has been detected please dry cover" etc. The processor 12 may be configured to increase the frequency of the tone to emphasize the urgency.

Figure 8:
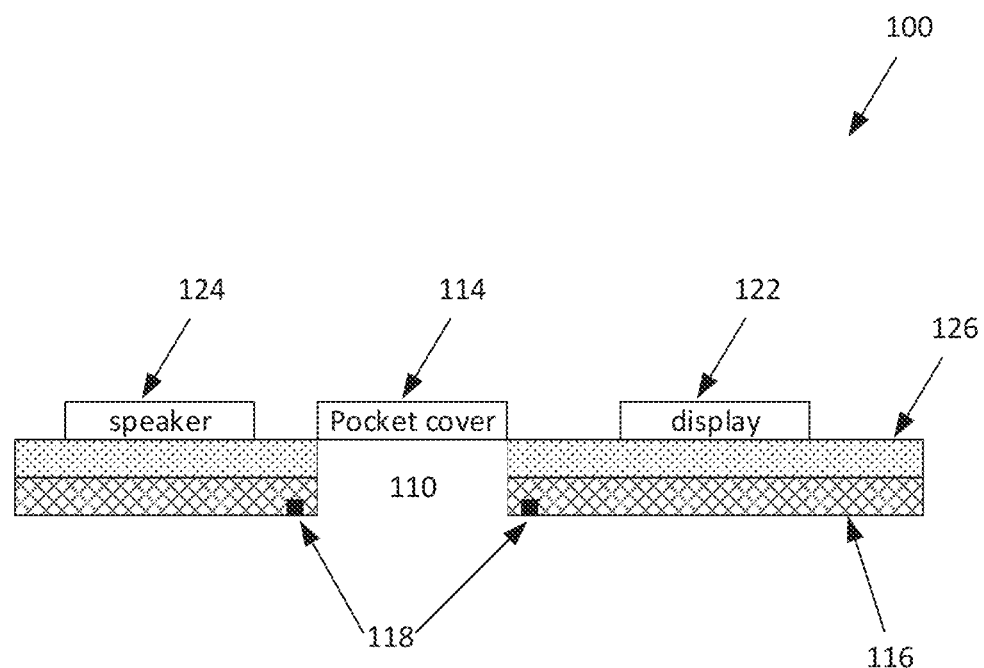
FIG. 8 is a cross sectional view of a protective cover in accordance with an embodiment.

FIG. 8 is a cross sectional view of a protective cover in accordance with an embodiment. As shown in the example of FIG. 8, the cover 100 includes the "smart" fabric 116 which includes the sensors 118 and a cutout 110 for covering and surrounding the catheter 112. The cover 100 may also include a waterproof layer 126 to protect the cover from water, hence allowing the patient to shower, perform water activities, etc. the display 122 and/or speaker 124 may be provided on the external layer 126 along with the pocket cover 114 which provides visual and physical access to the catheter area 110.

According to an embodiment, the smart fabric 116 and the external layer are made of a waterproof but breathable or perspirable material (i.e., that allows water vapor therethrough) that allows the skin to breathe and send out the moisture and sweat produced by the skin. An example of a suitable material for the external layer 126 may include polytetrafluoroethylene fabric, commonly referred to as Goretex®™ fabric.

According to an embodiment, a three-dimensional scanning of the body member to be covered is performed and fed to a computer system which determines the size and shape of each part of the protective cover such that the protective cover fits the body member in an optimized manner. A customized protective cover can thus be tailored on demand.

According to an embodiment, care or maintenance instructions for the protective cover can be provided as a label adhering to the inside of the protective cover, preferably without sewing any point that would puncture the cover and alter the waterproofness. Other information can be provided as printed labels or adhesive labels (e.g., size information).

According to an embodiment, the protective cover can be adapted in size and shape to fit a body member of an animal, such as a pet.

Although designed to cover a catheter insertion point, with or without a plaster, the protective cover 100 can be used to cover a small-scale injury and still allow the person to perform activities, i.e., in a military environment or in an emergency situation in which the person may need to cover the injury while being able to perform other activities.

According to another embodiment, the fabric described above in reference to the portions of the sleeve is not waterproof. Instead, the fabric is an elastic fabric that conforms particularly well to the surface of the body member. In such an embodiment, the seams and the edge of the openable window does not need to be particularly waterproof. In such a case, a kit can be provided, where the kit includes the non-waterproof embodiment of the protective cover 100, and an additional sleeve that covers the protective cover 100. This additional sleeve would be a tubular piece of waterproof fabric, such as polytetrafluoroethylene fabric, commonly referred to as Goretex™ fabric, and would be an open-ended tube that would comprise antiskid bands, preferably elastic or inflatable, at its proximal and distal ends (and thus similar to the analogous bands 212, 214). This additional sleeve, or over-sleeve, would be provided in a kit along with the protective cover 100 in its elastic version, and would be used to take a shower, while the more comfortable protective cover 100 (i.e., the non-waterproof alternative embodiment made of an elastic fabric) could be worn all day long and be protected from heavy water exposure by wearing the over-sleeve around it.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A protective cover for a body member of a patient having a catheter inserted therein at a catheter insertion point, the protective cover comprising a sleeve configured to wrap around the body member over the catheter, the sleeve comprising:
    a sleeve body configured for covering a surface of the body member of the patient including a joint, the sleeve body being made of a material that is non-rigid, flexible and elastic, the sleeve body conforming to the surface of the body member of the patient that is covered;
    an openable window for covering and providing access to the catheter when the protective cover is worn, the openable window being openable with respect to the sleeve body and defining an openable contour portion being fastenable to the sleeve body by a waterproof fastener along the openable contour portion which is waterproof along a whole length thereof, the openable window defining an inner surface and comprising an area on the inner surface for securing an antiseptic agent, wherein the inner surface of the openable window is applied onto the catheter insertion point when the openable window is closed, wherein the inner surface is brought away from the catheter insertion point when the openable window is opened,
    a proximal band and a distal band to be provided around the body member at a proximal end and a distal end of the sleeve body, respectively, each of the proximal band and the distal band being inflatable to press against the body member and provide waterproofness to the proximal end and to the distal end of the sleeve body, and
    wherein the protective cover is free of any rigid member covering the body member.

2. The protective cover of claim 1, further comprising a cutout pocket provided inside the openable window for receiving the catheter when the protective cover is worn by the patient, the cutout pocket comprising padding.

3. A protective cover for a body member of a patient having a catheter inserted therein at a catheter insertion point, the protective cover comprising a sleeve configured to wrap around the body part over the catheter, the sleeve comprising:
    a sleeve body configured for covering a surface of the body member of the patient including a joint, the sleeve body being made of a material that is non-rigid and flexible, the sleeve body conforming to the surface of the body member of the patient that is covered;
    an openable window for covering and providing access to the catheter when the protective cover is worn, the openable window being openable with respect to the sleeve body, the openable window defining an inner surface which is applied onto the catheter insertion point when the openable window is closed, and brought away from the catheter insertion point when the openable window is opened, wherein the openable window defines an openable contour portion being fastenable to the sleeve body by a waterproof fastener along the openable contour portion which is waterproof along a whole length thereof, the waterproof fastener comprises at least one of: a zipper, an autosealing pair of rubber bands, or a hook and loop fastener.

4. The protective cover of claim 3, wherein the openable window comprises an area on the inner surface for securing an antiseptic agent.

5. The protective cover of claim 3, further comprising a proximal band and a distal band to be provided around the body member at a proximal end and a distal end of the sleeve body, respectively, each of the proximal band and the distal band comprises an inner antiskid surface to press against the body member and remain thereon.

6. The protective cover of claim 5, wherein each of the proximal band and the distal band is inflatable to press against the body member and provide waterproofness to the proximal end and to the distal end of the sleeve body.

7. The protective cover of claim 3, further comprising a cutout pocket provided inside the openable window for receiving the catheter when the protective cover is worn by the patient.

8. The protective cover of claim 3, wherein the protective cover is free of any rigid member covering the body member.

9. The protective cover of claim 3, wherein the sleeve body and the openable window comprise an elastic fabric, further comprising an over-sleeve which is a waterproof tube to be provided in a kit with the protective cover and to be extended around the protective cover to protect the protective cover from water.

10. A protective cover for a body member of a patient having a catheter inserted therein at a catheter insertion point, the protective cover comprising a sleeve configured to wrap around the body member over the catheter, the sleeve comprising:
    a sleeve body configured for covering a surface of the body member of the patient, the sleeve body being made of a material that is non-rigid and flexible, the sleeve body conforming to the surface of the body member of the patient that is covered;
    a joint-covering portion for covering a joint of the body member and made of an elastic material; and
    an openable window for covering and providing access to the catheter when the protective cover is worn, the openable window being openable with respect to the sleeve body and the joint-covering portion, the openable window defining an inner surface and comprising an area on the inner surface for securing an antiseptic agent, wherein the inner surface of the openable window is applied onto the catheter insertion point when the openable window is closed, wherein the inner surface is brought away from the catheter insertion point when the openable window is opened, the sleeve body acting as an intermediate portion joining the joint-covering portion and the openable window in a watertight fashion when the openable window is closed, and wherein the protective cover is free of any rigid member covering the body member.

11. The protective cover of claim 10, further comprising antiskid bands at a first end and a second end of the sleeve for attaching the protective member to the body member.

12. The protective cover of claim 10, further comprising a cutout pocket provided in the fabric for receiving the catheter when the protective cover is worn by the patient.

13. The protective cover of claim 10, wherein the protective cover is free of any rigid member covering the body member.

* * * * *